(12) United States Patent
Imai et al.

(10) Patent No.: US 8,204,621 B2
(45) Date of Patent: Jun. 19, 2012

(54) TABLET DISCHARGING METHOD

(75) Inventors: Takafumi Imai, Toyonaka (JP); Akira Taniguchi, Toyonaka (JP)

(73) Assignee: Yuyama Mfg., Co., Ltd., Osaka (JP)

( * ) Notice: Subject to any disclaimer, the term of this patent is extended or adjusted under 35 U.S.C. 154(b) by 297 days.

(21) Appl. No.: 12/665,470

(22) PCT Filed: Jun. 16, 2008

(86) PCT No.: PCT/JP2008/060961
§ 371 (c)(1),
(2), (4) Date: Dec. 18, 2009

(87) PCT Pub. No.: WO2008/156047
PCT Pub. Date: Dec. 24, 2008

(65) Prior Publication Data
US 2010/0181334 A1    Jul. 22, 2010

(30) Foreign Application Priority Data
Jun. 21, 2007   (JP) ................................ 2007-164047

(51) Int. Cl.
*G06F 17/00* (2006.01)
(52) U.S. Cl. ........ 700/240; 700/233; 700/236; 700/242; 221/241
(58) Field of Classification Search .................. 700/240, 700/236, 241, 242, 233; 221/241, 304
See application file for complete search history.

(56) References Cited

U.S. PATENT DOCUMENTS

| | | | | |
|---|---|---|---|---|
| 5,337,919 A | * | 8/1994 | Spaulding et al. | 221/13 |
| 5,907,493 A | * | 5/1999 | Boyer et al. | 700/241 |
| 6,478,185 B2 | * | 11/2002 | Kodama et al. | 221/13 |
| 7,831,334 B2 | * | 11/2010 | Vollm et al. | 700/228 |
| 7,912,578 B1 | * | 3/2011 | Frankel | 700/240 |
| 7,912,582 B1 | * | 3/2011 | Holtje et al. | 700/242 |

FOREIGN PATENT DOCUMENTS

| | | |
|---|---|---|
| JP | 9215729 A | 8/1997 |
| JP | 2002029511 A | 1/2002 |

* cited by examiner

*Primary Examiner* — Timothy Waggoner
(74) *Attorney, Agent, or Firm* — Jones Day

(57) ABSTRACT

There is provided a tablet discharging method capable of discharging a vial to an outlet corresponding to a size of the vial even if the size of the vial is changed. The tablet discharging method is related to removing a vial from a stocker accommodating a large number of vials according to a prescription data, dispensing tablets into the vial to fill the vial and discharging the vial filled with the tablets. The tablet discharging method includes the following steps of: determining a vial of an appropriate size according to a prescription data; checking for a stock of the determined vial; fixing a size by changing the determined vial to a vial of a size larger than that of the determined vial when the vial of the determined size is out-of-stock; and discharging the vial filled with the tablets to an outlet holding the vial of the fixed size.

2 Claims, 20 Drawing Sheets

FIG. 9
(a)
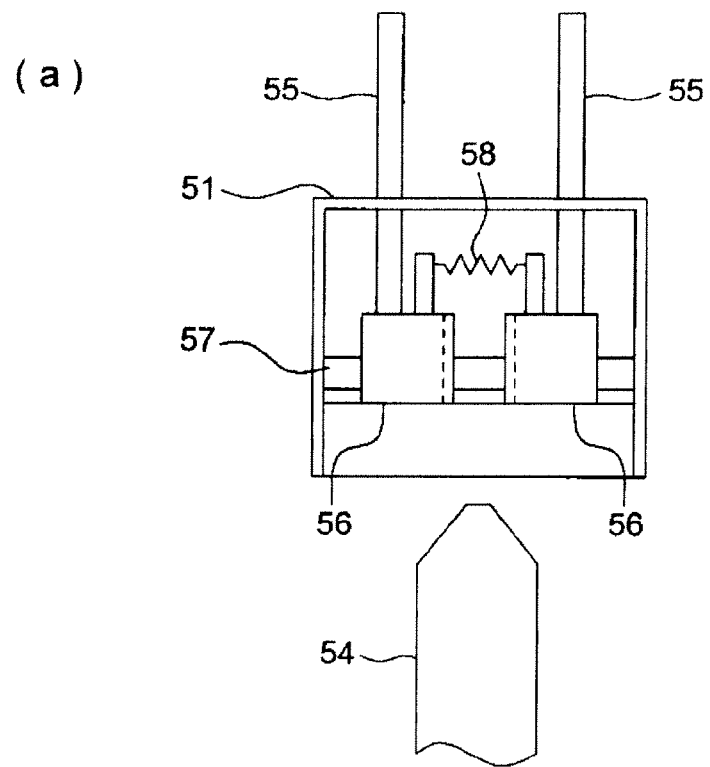
(b)
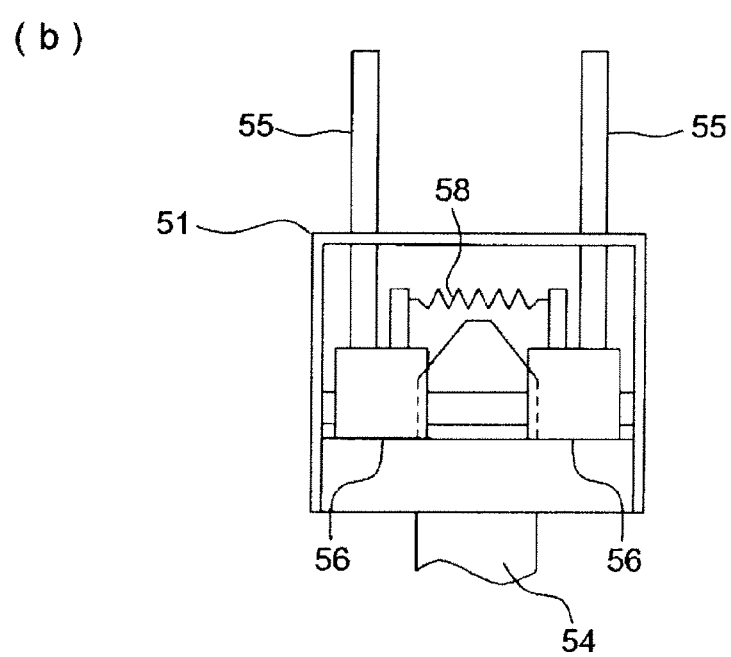

TABLET DISCHARGING METHOD

CROSS REFERENCE TO RELATED APPLICATIONS

This application is a 35 U.S.C §371 national stage filling of International Application No. PCT/JP2008/060961, filed Jun. 16, 2008, the entire contents of which are incorporated by reference herein, which claims priority to Japanese Patent Application No. 2007-164047, filed Jun. 21, 2007, the entire contents of which are incorporated by reference herein.

TECHNICAL FIELD

The present invention relates to a tablet discharging method of filling a vial with tablets and discharging the vial.

BACKGROUND ART

There exists in the art a tablet filling device configured to dispense tablets according to prescription data, fill a vial with the tablets, and discharge the vial filled with the tablets to an outlet. Such a tablet filling device is configured such that stockers accommodate a large number of vials according to their size. Further, when the prescription data arrives, the vials of a size suitable to a prescription of the prescription data are removed one by one.

The below-mentioned reference, Patent Document 1, suggests that during removing a vial from a stocker according to the order of removal, when it is determined that a vial of a corresponding size is out-of-stock, a vial with a size larger than that of the out-of-stock vial is supplied. Further, when there are no larger-sized tablet containers, removal of the vial stops.

Outlets of a tablet filling device disclosed in Patent Document 1 can hold the vials irrespective of their size. Thus, the outlets can hold the vials even if a small-sized vial is changed to a large-sized one. However, in case of a tablet filling device wherein outlets are arranged depending on the size of a vial, there is a problem in that when a small-sized vial is changed to a large-sized one after initiating its operation, the large-sized one cannot be discharged to an initially-arranged outlet for the small-sized vial.

Patent Document 1: Japanese Patent Application Laid-Open No. 2002-29511

SUMMARY OF THE INVENTION

Thus, it is an object of the present invention to provide a tablet discharging method, which allows a vial to be discharged through an outlet corresponding to a size of the vial even if the size of the vial is changed.

In order to solve the foregoing problems, according to the present invention, there is provided a tablet discharging method of removing a vial from a stocker accommodating a large number of vials according to a prescription data, dispensing tablets into the vial to fill the vial, and discharging the vial filled with the tablets. The tablet discharging method includes the following steps: determining a vial of an appropriate size according to the prescription data; checking for a stock of the determined vial; fixing a size by changing the determined vial to a vial of a size larger than that of the determined vial when the vial of the determined size is out-of-stock; and discharging the vial filled with the tablets to an outlet holding the vial of the fixed size.

According to the method, when the vial of the appropriate size is out-of-stock after the vial is determined according to the prescription data, a size of the vial is fixed as being larger than that of the determined vial. Thus, the changed vial can be discharged not to an outlet holding the vial of the initially-determined size, but to an outlet holding the vial of the later-fixed size.

Preferably, the step of checking for a stock of the determined vial is performed in at least one of the following: when an error relating to label application occurs at step of applying a label to the vial; and when it is detected that the tablets are out-of-stock at step of supplying the tablets to the vial. When the error relating to label application occurs, it is necessary to apply a label to a new vial. In such a case, even if the vial is out-of-stock, a size of the vial is fixed as being larger than that of the out-of-stock vial. Further, when the tablets are out-of-stock, it is necessary to fill a new vial with the tablets after replenishing the tablets. In this case, even if the vial is out-of-stock, a size of the vial is fixed as being larger than that of the out-of-stock vial.

According to the present invention, a vial can be discharged to an outlet corresponding to a size of the vial even if the size of the vial is changed.

BRIEF DESCRIPTION OF THE DRAWINGS

FIGS. 9(a) and 9(b) are side views showing operations of movable blocks for pins and a pin opening/closing bar.

DESCRIPTION OF REFERENCE NUMERALS

1 . . . Tablet filling device
9 . . . Vial
21 . . . Stocker
113 . . . Outlet

DETAILED DESCRIPTION

Figure 1:
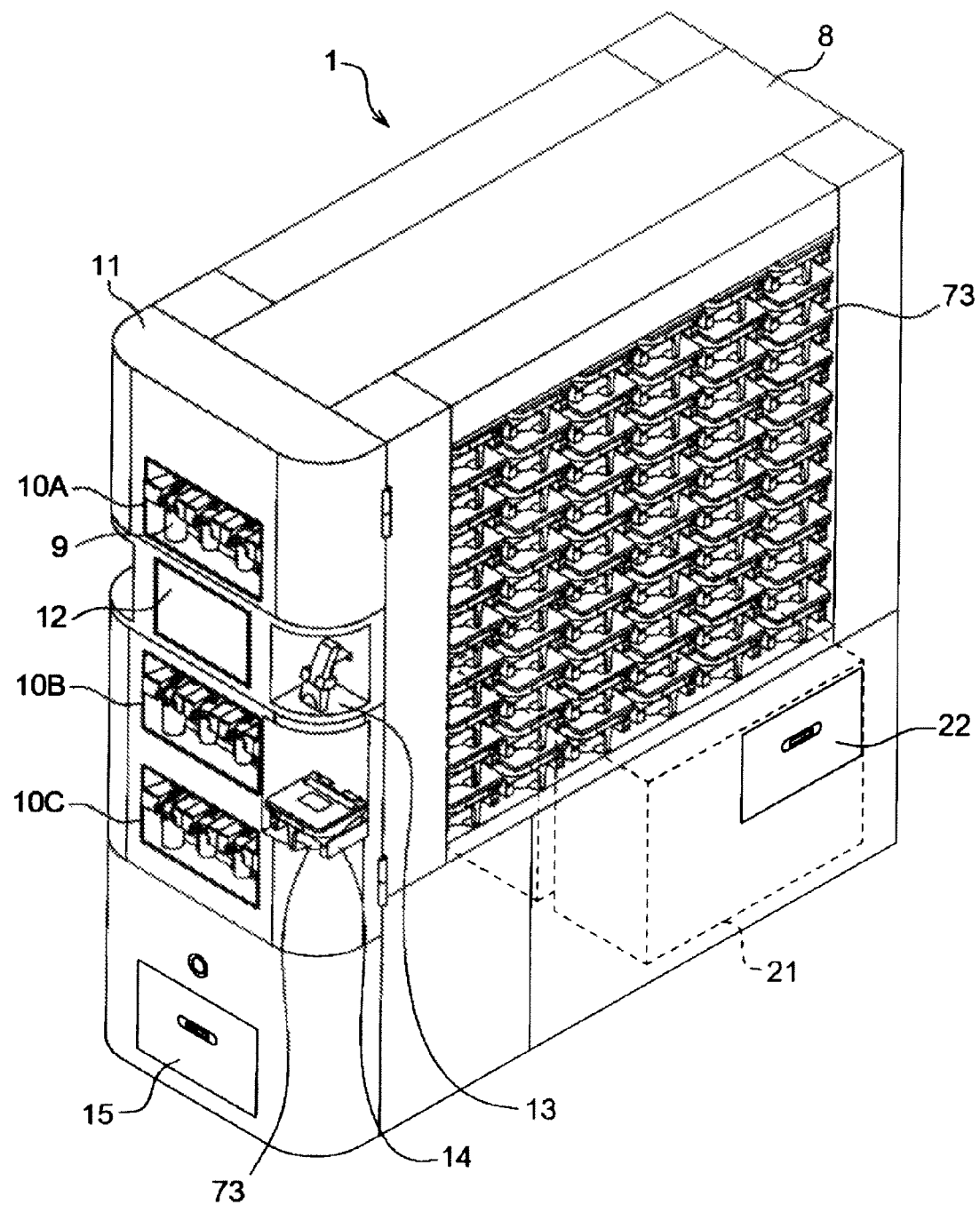
FIG. 1 is a perspective view of a tablet filling device according to the present invention.
Figure 2:
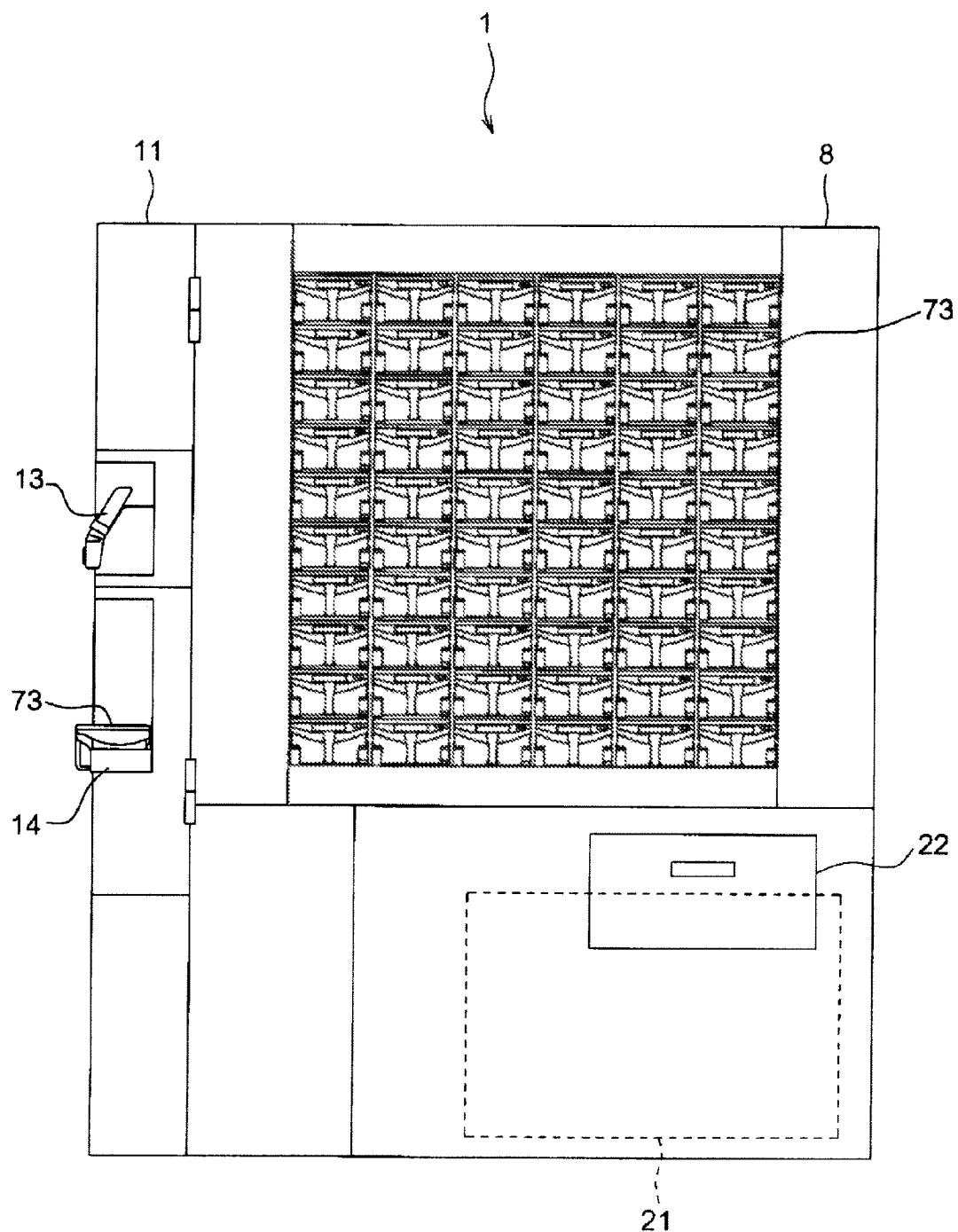
FIG. 2 is a side view of the tablet filling device shown in FIG. 1.
Figure 3:
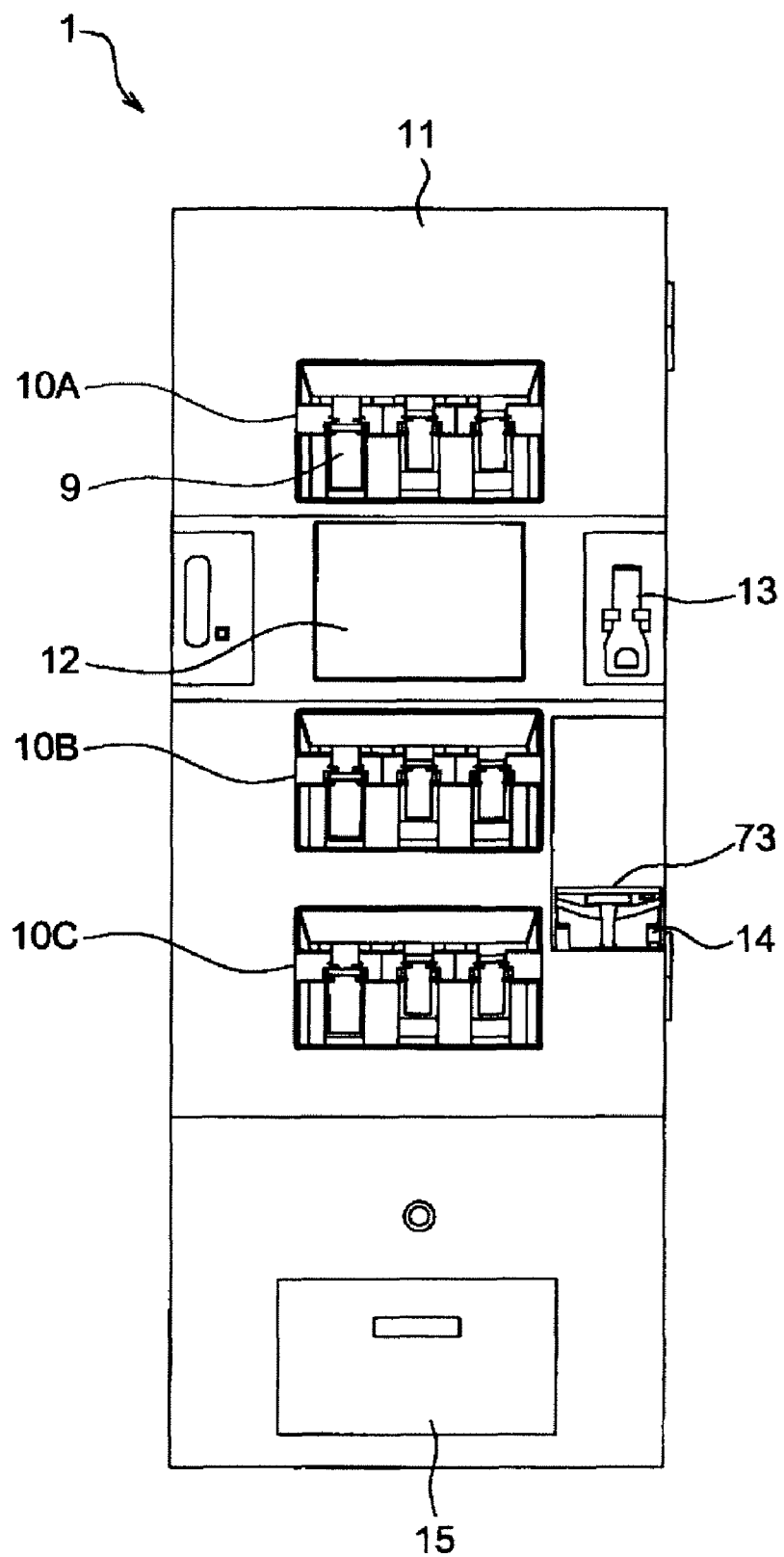
FIG. 3 is a front view of the tablet filling device shown in FIG. 1.
Figure 4:
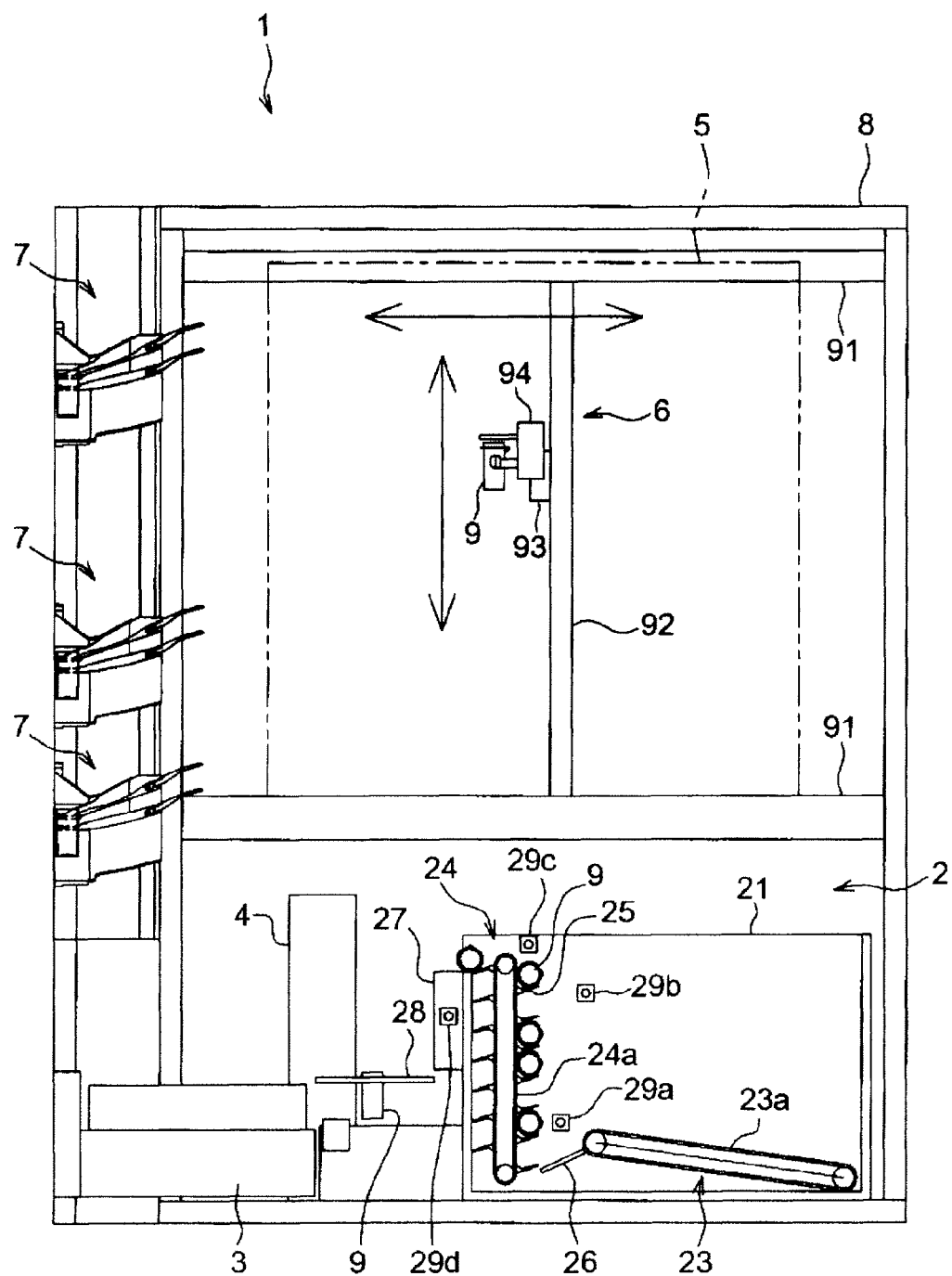
FIG. 4 is a side sectional view of the tablet filling device shown in FIG. 1.

FIGS. 1 to 4 illustrate a tablet filling device 1 according to an embodiment of the present invention. As shown in FIG. 4, the tablet filling device 1 includes a vial supplying unit 2, a labeling unit 3, a vial lifter 4, a tablet supplying unit 5, a conveying unit 6 and a discharging unit 7. The tablet filling device 1 has a device body 8. Herein, a face of the device body 8, at which discharging windows 10A, 10B and 10C for vials 9 are disposed, is referred to as a front.

A front door 11 is openably and closably provided in the front of the device body 8. The discharging windows 10A, 10B, 10C open along vertical three locations in the front door 11. Further, an operation panel 12 is provided between the upper discharging window 10A and the middle discharging window 10B. A barcode reader 13 is provided at the right side of the operation panel 12. An auxiliary mount 14 for replenishing or returning of tablets is provided below the barcode reader 13. A drawer for pulling out the labeling unit 3 is provided below the lower discharging window 10C.

Figure 5:
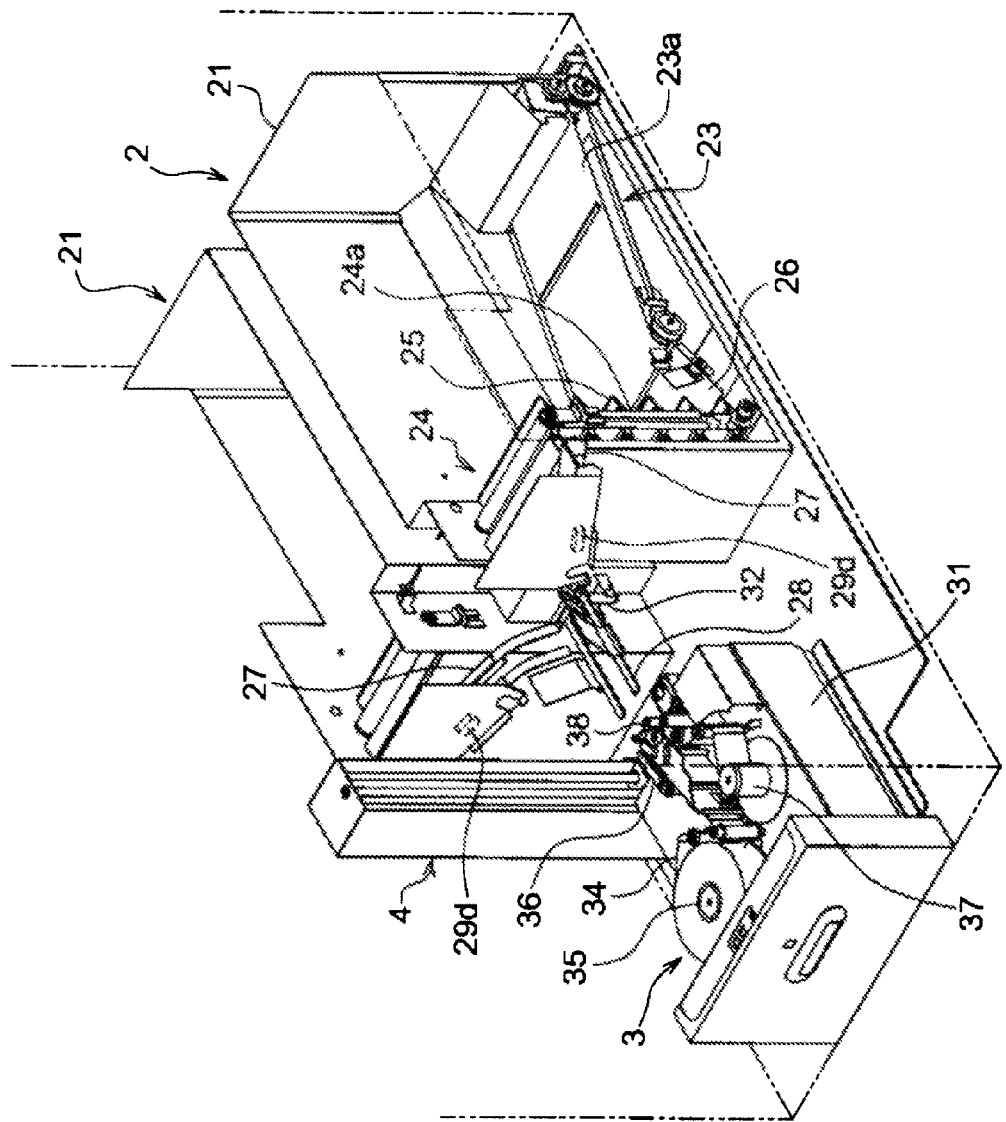
FIG. 5 is a perspective view of a vial supplying unit, a labeling unit and a vial lifter.

<Vial supplying unit 2> As shown in FIG. 5, the vial supplying unit 2 has stockers 21 of a rectangular box shape. The stockers are disposed at both lateral sides of a lower inside of the device body 8 when viewed from the front of the device body 8. Each of the stockers 21 randomly stocks the vials 9 of different sizes therein. The vials 9 may be replenished after opening doors 22 (see FIG. 1) provided at right and left sides of the device body 8. A conveyer 23, which includes an endless belt 23a to be driven in a traveling manner, is provided on an inside bottom of each of the stockers 21 as slanting upward toward the front of the device body 8. The conveyer 23 is configured to convey the vials 9 stocked in the stocker 21 toward the front. A removal device 24 is vertically disposed alongside an inner wall of a front side of the stocker 21. The removal device 24 includes an endless belt 24a to be driven in a traveling manner, to which paddles 25 are attached at regular intervals. The vial 9 is transversely held by the paddle 25 and can be removed along with ascent of the endless belt 24a. A guide plate 26, which guides the vials 9 having been conveyed by the conveyer 23 to the paddles 25 of the removal device 24, is provided between a front end of the conveyer 23 and a lower end of the removal device 24.

Figure 6:
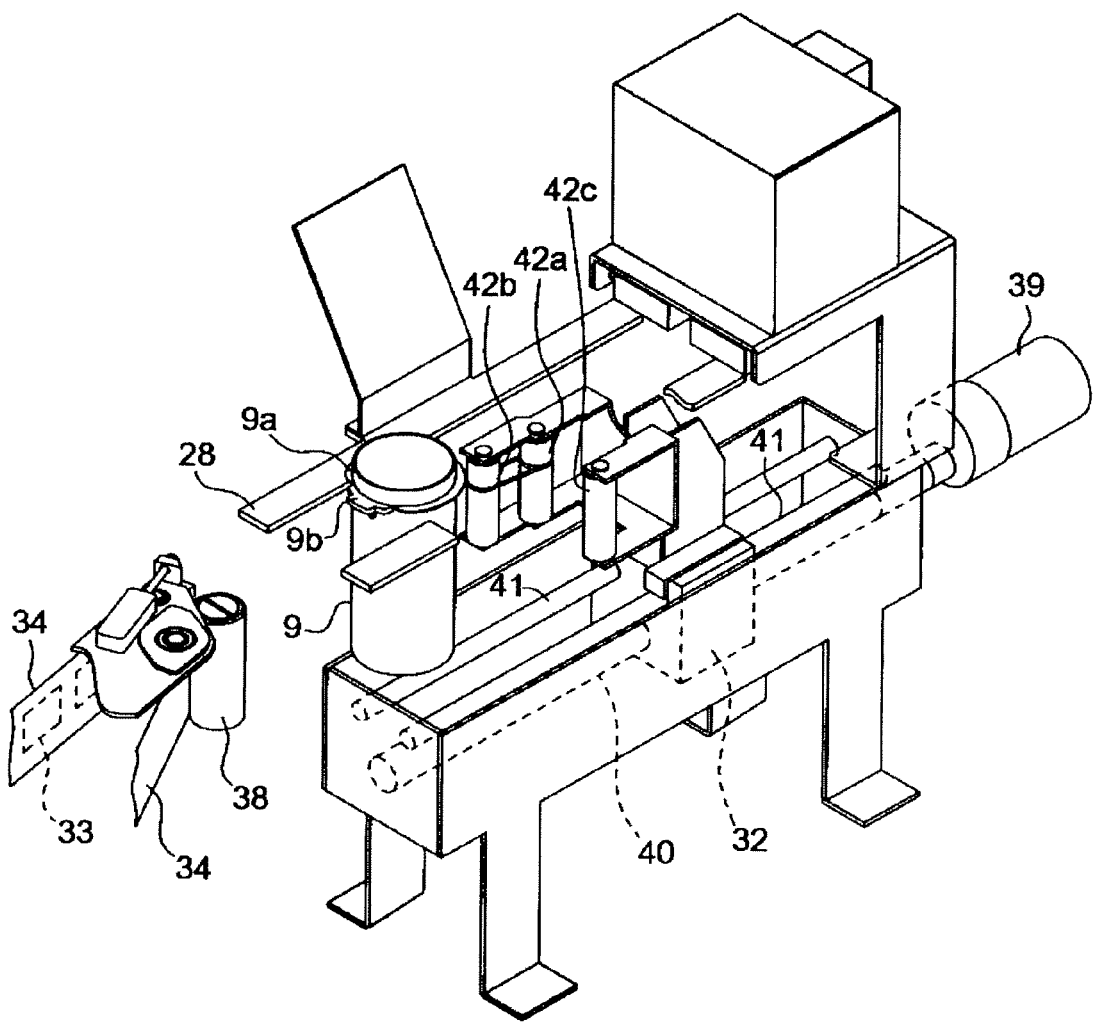
FIG. 6 is a perspective view of the labeling unit.

A pair of chutes 27 for sliding down the vial 9 having been removed from the stockers 21 by means of the removal device 24 and a pair of forks 28 for receiving and supporting the vial 9 having slid down from the pair of chutes 27 are provided at front outer walls of the stockers 21. The forks 28 are configured to vary a horizontal width therebetween so as to support any one of the vials 9 of different sizes by means of the well-known mechanism such as a rack-and-pinion mechanism. Further, as shown in FIG. 6, the vial 9 has a flange 9a around an outer periphery of its opening and a protruding piece 9b having a mechanism for locking a cap (not shown).

As shown in FIG. 4, the vial supplying unit 2 has the following sensors: a stockout sensor 29a at a lower inside of each of the stockers 21; an overfill sensor 29b at an upper inside of each of the stockers; a preparation detecting sensor 29c for detecting the vial 9 held by the paddle 25 in a topmost position; and a vial waiting sensor 29d for detecting the vial 9 staying stopped on the chute 27 by a stopper (not shown).

Figure 7:
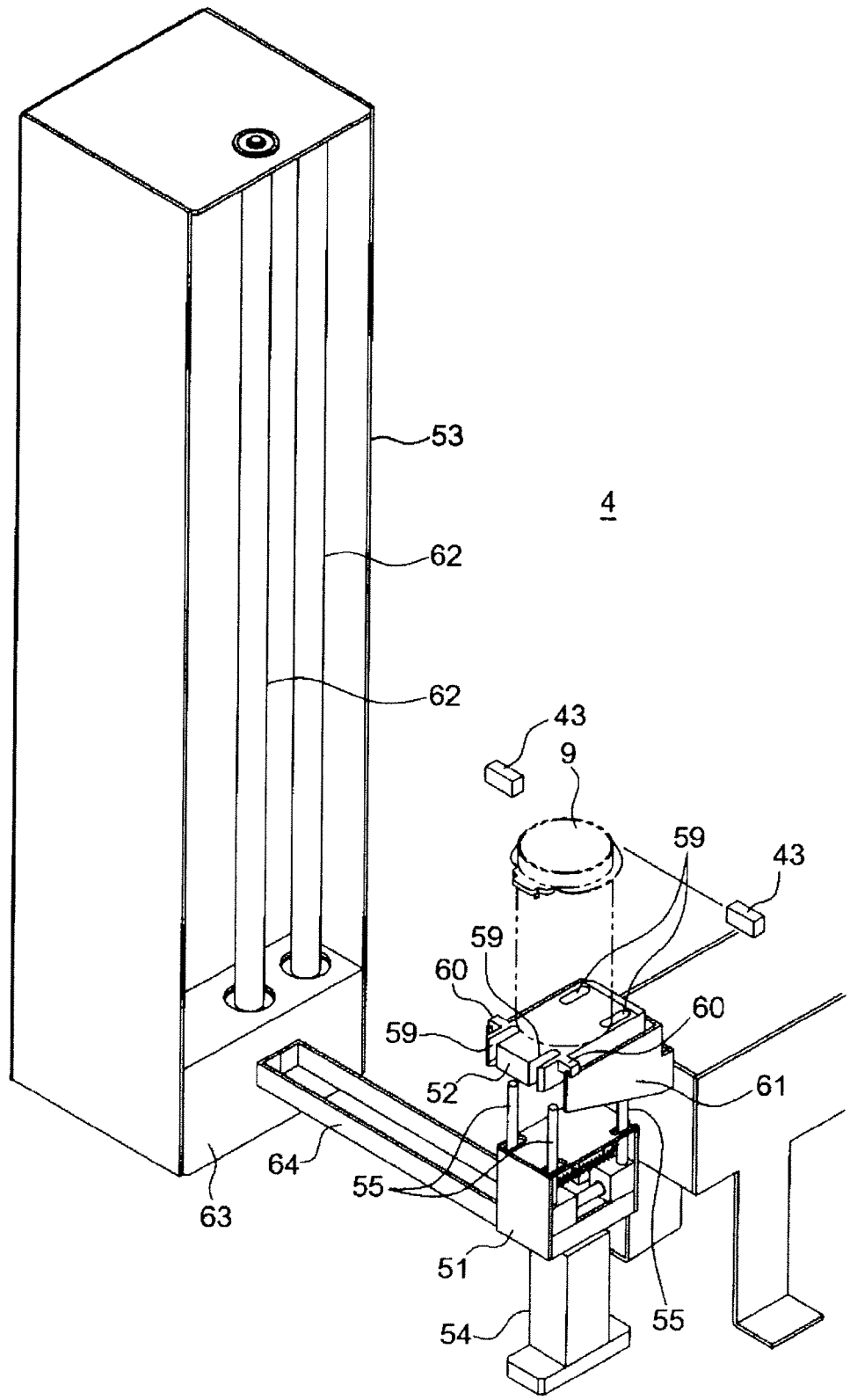
FIG. 7 is a perspective view of the vial lifter, showing that a lifting table stays in a standby position.

<Labeling unit 3> As shown in FIG. 5, the labeling unit 3 includes a label printer 31 and a pusher 32. As shown in FIG. 6, the label printer 31 uses a label tape 34, on which labels 33 to be applied on an outer periphery of the vial 9 are adhered at regular intervals. As shown in FIG. 5, the label printer 31 includes the following: a tape reel 35 around which the label tape 34 winds; a print head 36 for printing information such as a prescription number, a patient name and a medicine name on the label 33 of the label tape 34 fed from the tape reel 35; a take-up reel 37 for taking up the label tape 34 from which the label 33 is removed; and a driving roller 38 for rotating the vial 9. The label printer may comprise a conventional label printer. As shown in FIG. 6, the pusher 32 is movable along a guide rod 41 and parallel to the forks 28 by means of a ball screw 40 driven by a motor 39. The pusher 32 has three rollers 42a, 42b, 42c, which press the vial 9 supported by the forks 28 of the vial supplying unit 2 against the driving roller 38 of the label printer 31. As shown in FIG. 7, sensors 43 for detecting a position of the protruding piece 9b of the vial 9 of a large or small size are provided in the device body 8.

Figure 8:
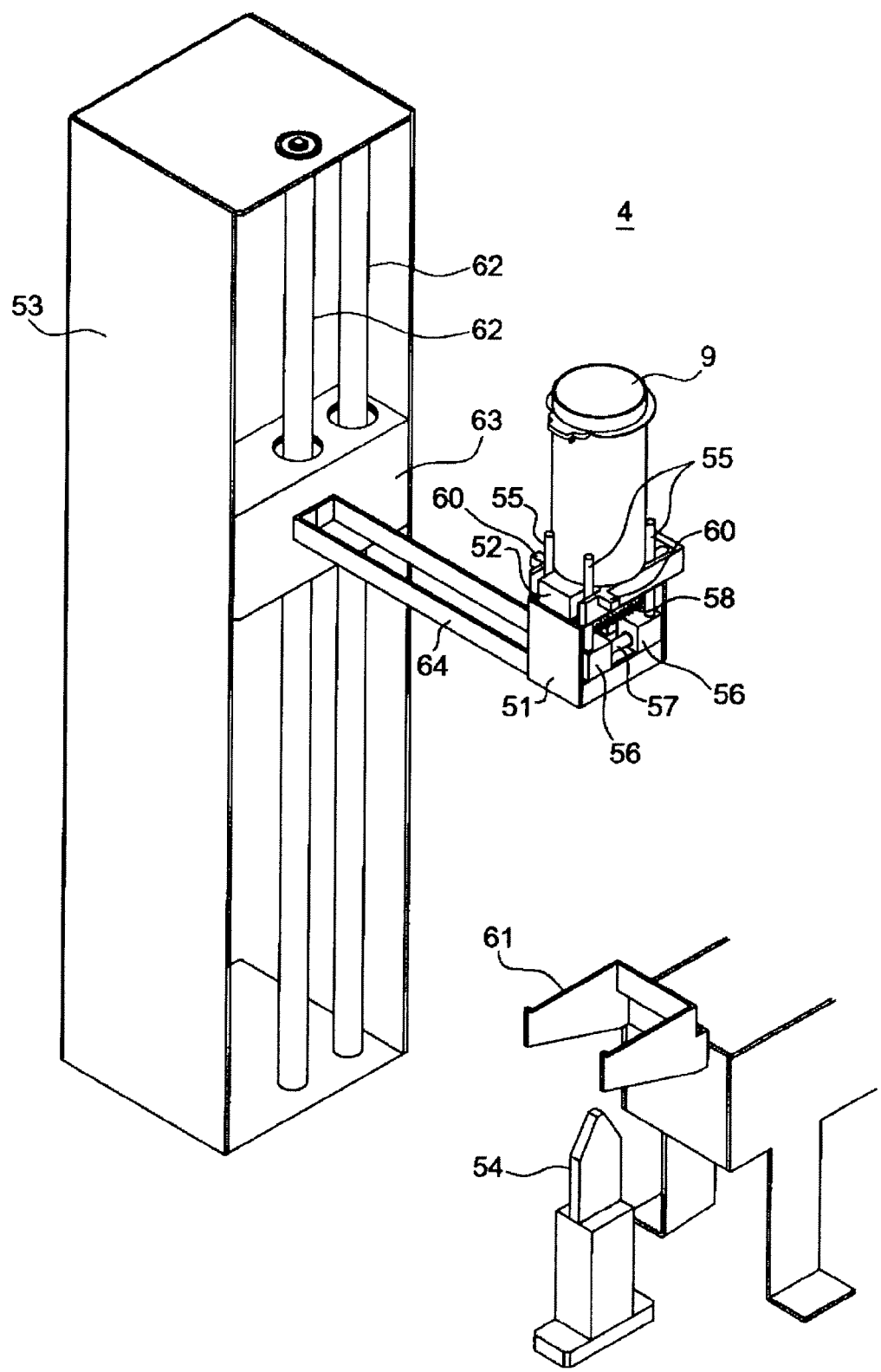
FIG. 8 is a perspective view of the vial lifter, showing that the lifting table is moving upward.
Figure 10:
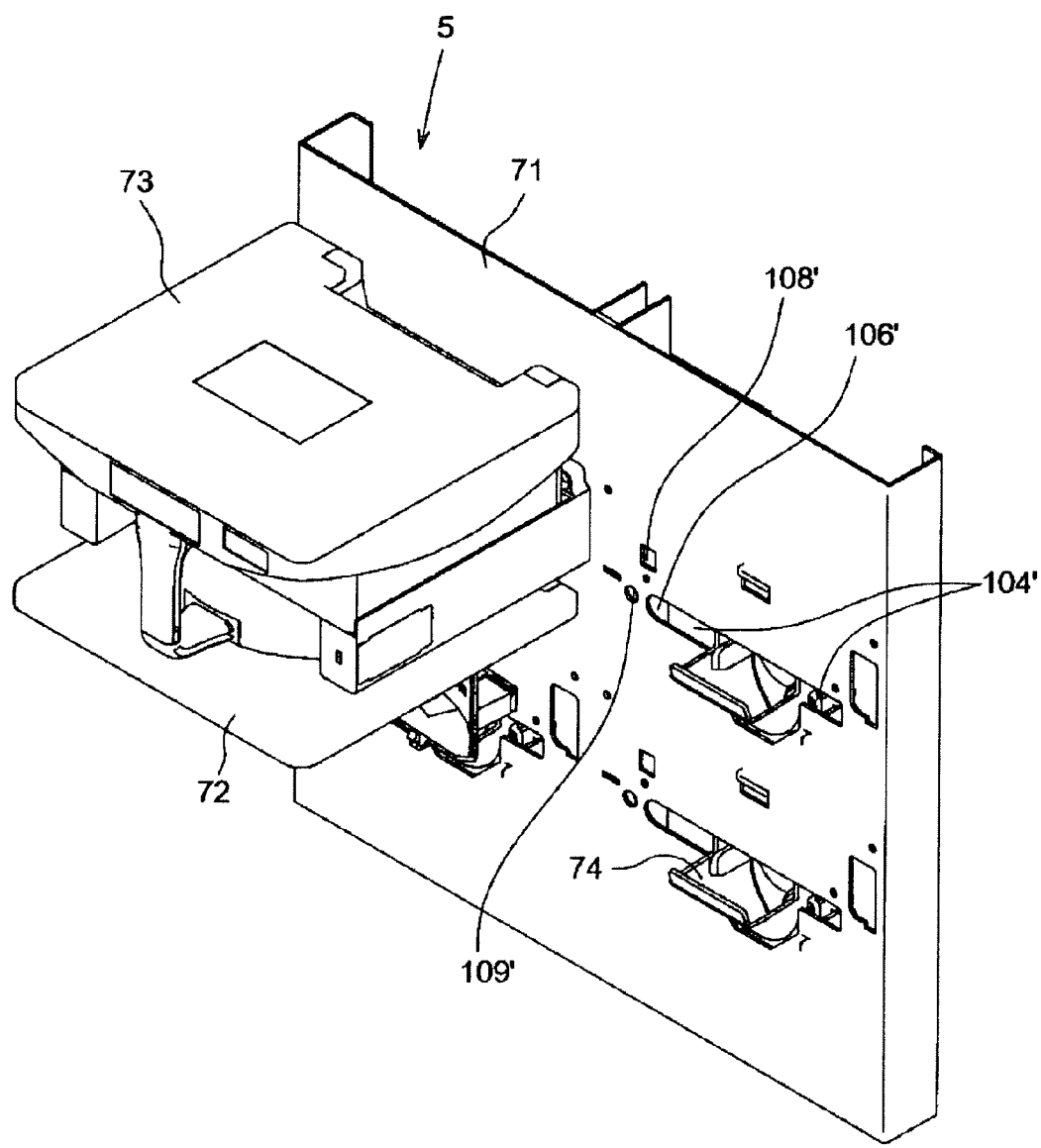
FIG. 10 is a perspective view of a tablet supplying unit.

<Vial lifter 4> As shown in FIGS. 7 to 9, the vial lifter 4 includes the following: a lifting table 51 for placing the vial 9 thereon; a supporting plate 52 disposed on the lifting table 51; a lifting mechanism 53 for lifting and lowering the lifting table 51 and the supporting plate 52; and a pin opening/closing bar 54.

The lifting table 51 has four pins 55 projecting upward for holding the outer periphery of the vial 9 on its top side. Bases of two opposite pins 55 are fixed to movable blocks 56. Two movable blocks 56 are movable in opposite directions toward and away from each other along a guide rod 57. The two movable blocks are biased in the direction toward each other by a spring 58. The supporting plate 52 has elongated cutouts 59 through which the four pins 55 pass. The supporting plate 52 has a plurality of lugs 60 at its outer periphery. The supporting plate 52 is configured to be placed on a bracket 61 fixed to the device body 8 through the lugs 60. The lifting mechanism 53 has a lifting block 63 that is lifted and lowered along guide rods 62 by a belt driving device (not shown). The lifting table 51 is fixed to a distal end of an arm 64 that is provided at the lifting block 63. The pin opening/closing bar 54 is located below the lifting table 51 and is fixed to the device body 8. The pin opening/closing bar 54 engages and disengages from a space between the two movable blocks 56 of the lifting table 51 along with lifting and lowering movements of the lifting table 51 to thereby move the movable blocks 56 to open and close the four pins 55.

As the lifting table 51 is lowered by operation of the lifting mechanism 53 of the vial lifter 4, as shown in FIG. 7, the four pins 55 are pushed out and widened by the pin opening/closing bar 54 located below the lifting table 51 and is then moved in the direction away from the vial 9 against a biasing force of the springs 58. During the lowering movement of the lifting table 51, the supporting plate 52 stops by being hung up by the bracket 61, whereas the lifting table 51 continues to go down and stops at a bottommost position. As the lifting table 51 moves upward from the bottommost position, as shown in FIG. 8, the supporting plate 52 hung up by the bracket 61 is placed on the lifting table. Further, the four pins 55 are disengaged from the pin opening/closing bar 54, thereby pressing and holding the vial 9 placed on the supporting plate 52 under the biasing force of the springs 58. The lifting mechanism 53 conveys the vial 9 placed on the lifting table 51 from a labeling position to a delivery position of the conveying unit 6, which will be described below.

Figure 11:
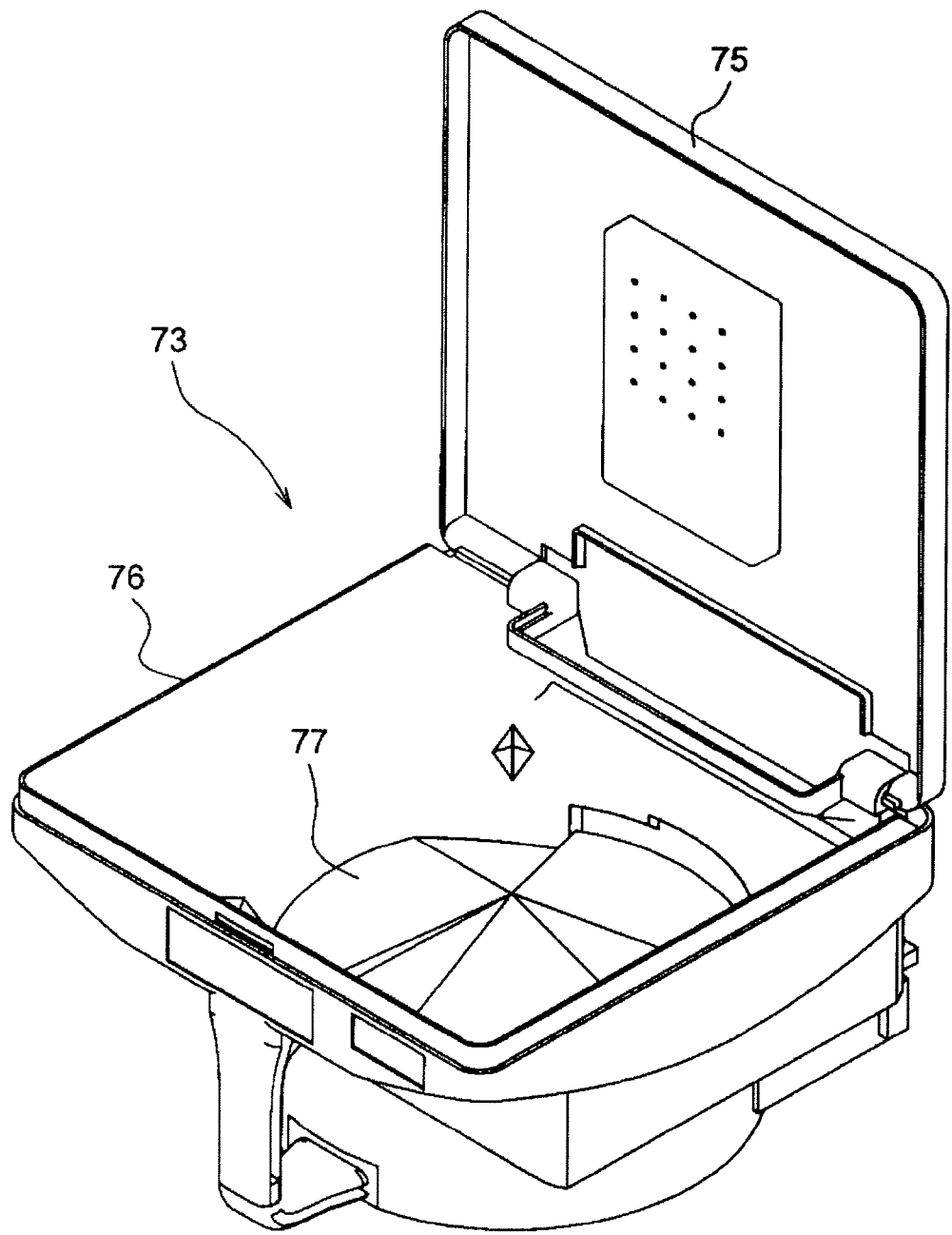
FIG. 11 is an upper perspective view of a tablet cassette.
Figure 12:
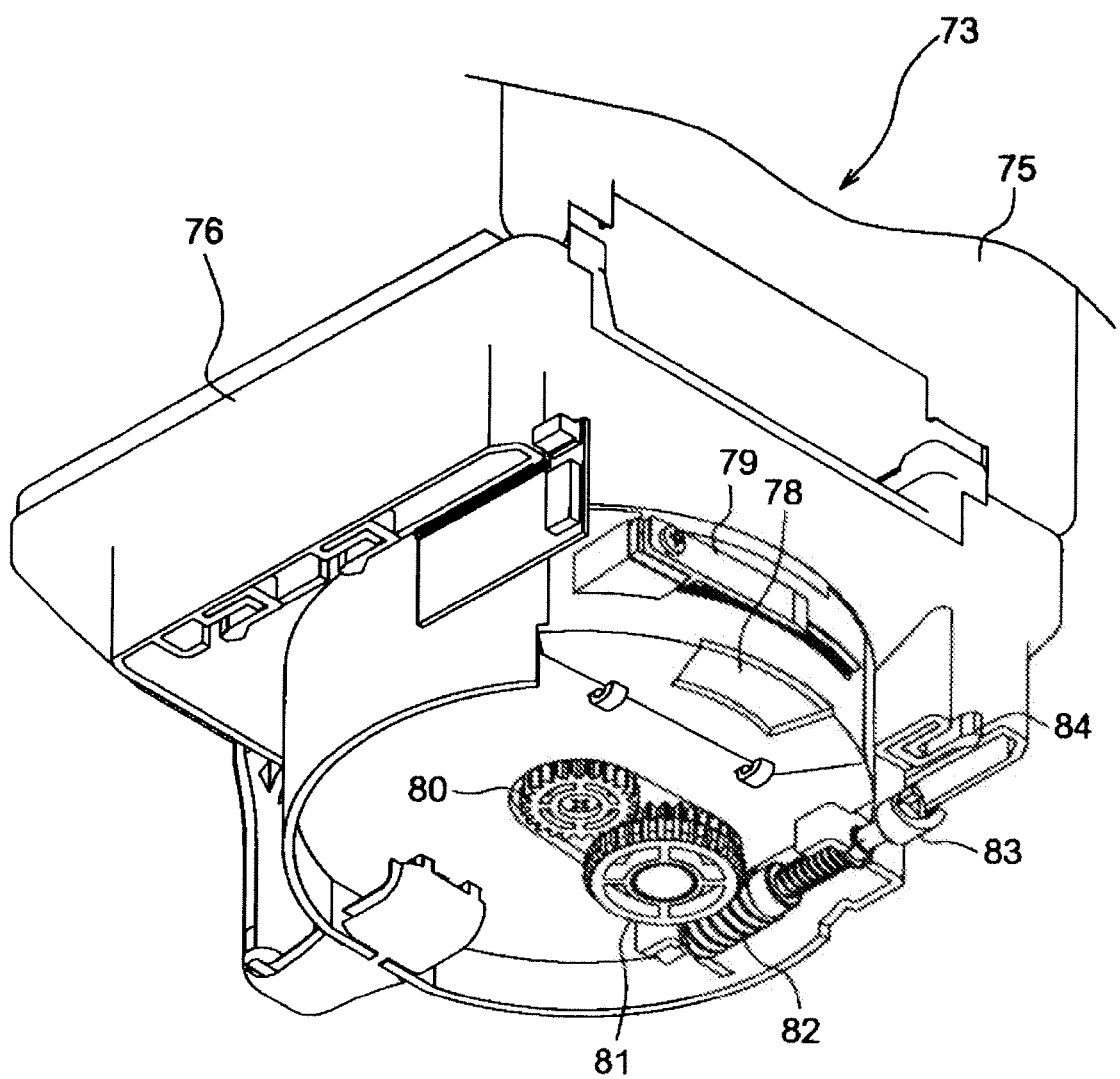
FIG. 12 is a lower perspective view of the tablet cassette.

<Tablet supplying unit 5> The tablet supplying unit 5 includes a large number of tablet cassettes 73, which are detachably attached to attaching mounts 72 provided on supporting panels 71 disposed along both sides of the device body 8. Each of the supporting panels 71 has tablet outlets 74 that are positioned to correspond to the tablet cassettes 73, respectively. Each of the supporting panels further has sensor holes 104', driving shaft holes 106', protruding piece holes 108' and detection rod holes 109', in which count sensors 104, driving shafts 106, protruding pieces 108 and detecting rods 109 of an arm unit 94 described below are put, respectively. As shown in FIG. 11, the tablet cassette 73 includes a tablet container 76 with a lid 75 openably and closably attached thereto. A rotor 77 is rotatably attached to an inner bottom of the tablet container 76. The rotor 77 has pockets (not shown) for holding tablets at its outer periphery, which extend in an axial direction and are juxtaposed at regular intervals in a peripheral direction. As shown in FIG. 12, the tablet container 76 has a discharging hole 78 defined at its outer bottom and communicating with one of the pockets of the rotor 77. A partition member 79 is provided above the discharging hole 78 for partitioning the pocket of the rotor 77 and discharging a bottommost tablet among the tablets held in the pocket through the discharging hole 78. In a center of the outer bottom of the tablet container 76, a rotor gear 80 is coupled to a rotating shaft of the rotor 77 penetrating through the bottom of the tablet container 76. Further, an intermediate gear 81 meshed with the rotor gear 80 and a worm gear 82 meshed with the intermediate gear 81 are attached to the outer bottom of the tablet container 76. The worm gear 82 has an engaging receptacle 83, which engages an engaging portion 107 of a driving shaft 106 of the conveying unit 6 (which will be described below) to receive power therefrom, at its tip end. The tablet container 76 further has an engaging portion 84 adjacent to the engaging receptacle 83 at its back side.

<Conveying unit 6> As shown in FIG. 4, the conveying unit 6 is disposed between the tablet supplying units 5 arranged at the both sides of the device body. The conveying unit includes the following: first horizontal rails 91 fixed to an upper side and a lower side of the device body 8; a vertical rail 92 forward and backward movably mounted to the first horizontal rails 91; a second horizontal rail 93 vertically movably mounted on the vertical rail 92; and the arm unit 94 laterally movably mounted on the second horizontal rail 93.

Figure 13:
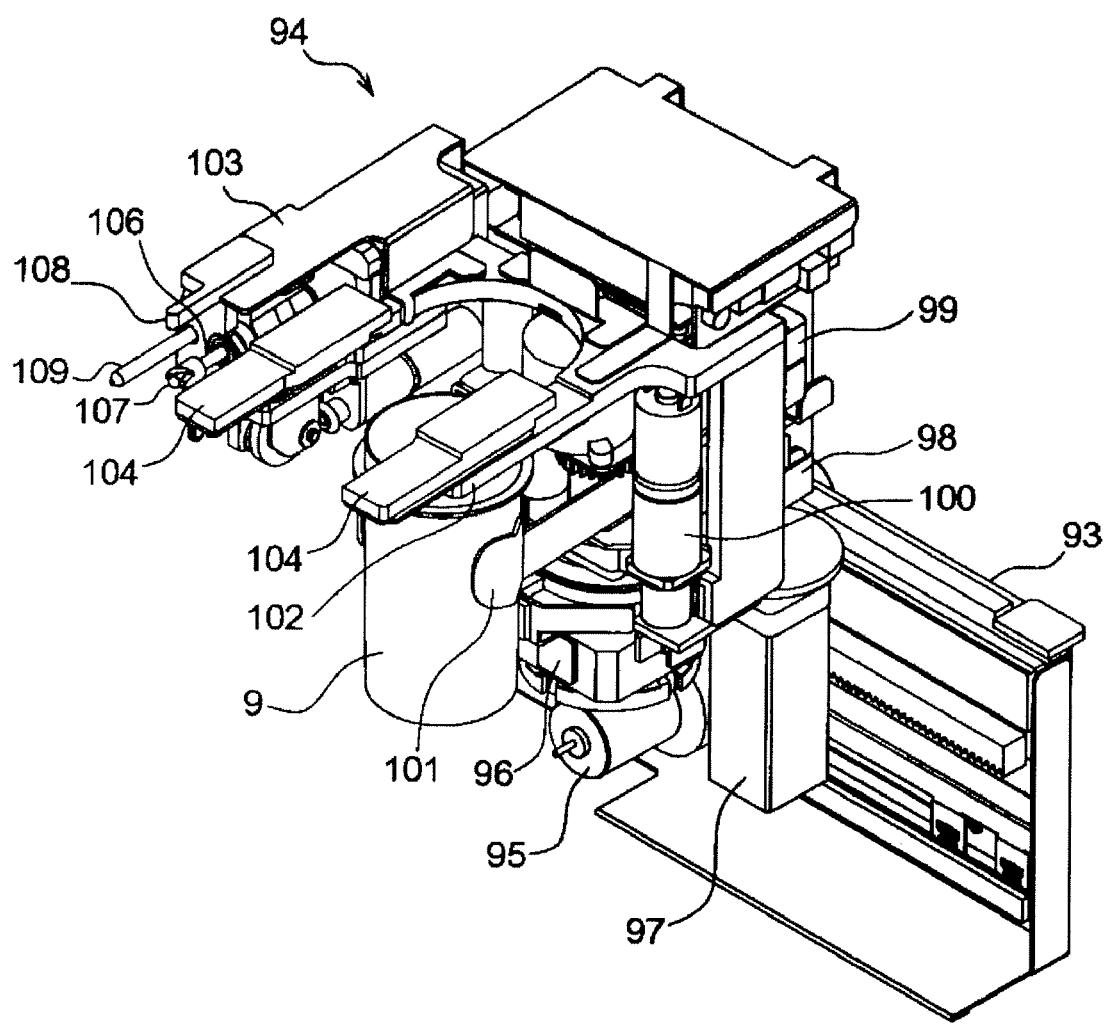
FIG. 13 is a perspective view of an arm unit of a conveying unit.
Figure 14:
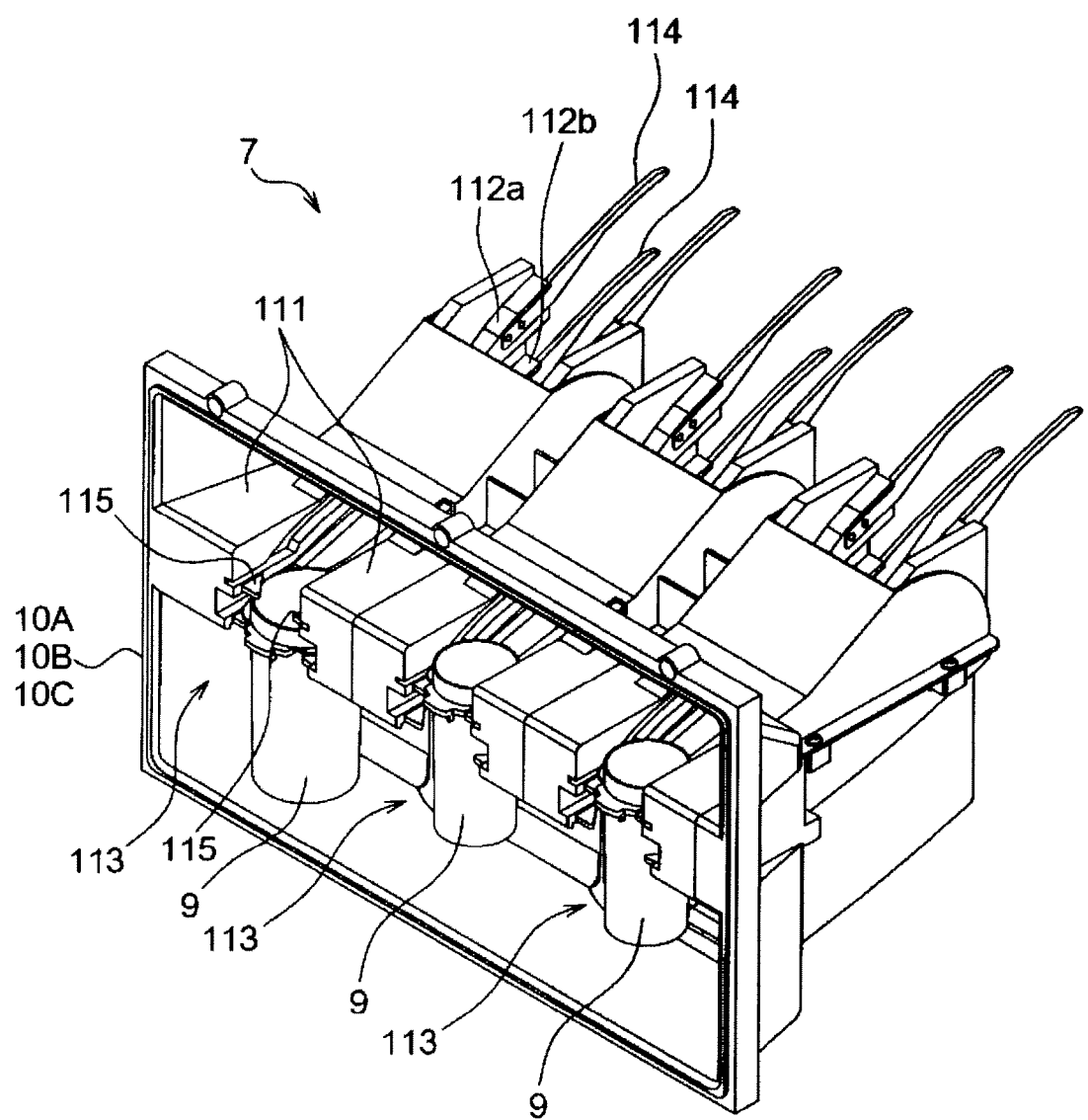
FIG. 14 is a perspective view of a discharging unit.

As shown in FIG. 13, the arm unit 94 includes the following: an orthogonal moving base 96 mounted on the second horizontal rail 93 to be moved by a motor 95; a pivoting base 98 mounted on the orthogonal moving base 96 to be pivoted by a motor 97; and a tilting base 99 mounted on the pivoting base 98 to be tilted by a motor (not shown). A pair of arms 101, which are openable and closable by operation of a motor 100 to grip and release the vial 9, are attached to the tilting base 99. A U-shaped sensor arm 102 and a driving arm 103 are provided in the pivoting base 98 above the arms 101. The count sensors 104 are attached to both distal ends of the U-shaped sensor arm 102 to count the number of the tablets discharged from the tablet cassette 73. The driving shaft 106, which is driven by a motor to rotate, is provided in the driving arm 103. The driving shaft 106 has the engaging portion 107, which engages the above-described engaging receptacle 83 of the worm gear 82 of the tablet cassette 73, at its tip end. Further, the protruding piece 108, which engages the engaging portion 84 of the tablet cassette 73 to position the arm unit 94 in a proper place, and the detection rod 109, which detects whether the arm unit 94 is positioned in the proper place, are attached to the driving arm 103.

<Discharging unit 7> The discharging unit 7 includes nine pairs of holding members 111, each of which bilaterally lies to makes one pair. Three pairs of the holding members 111 are disposed at each of the three discharging windows 10A, 10B, 10C. Two slopes 112a, 112b, which are juxtaposed vertically, are provided at one of the opposite sides in one pair of the holding members 111. Upper ends of the slopes are located within the device body 8 and lower ends of the slopes are located in the discharging window 10A, 10B, 10C, thereby forming an outlet 113. A guiding member 114 further extending obliquely upward is attached to the upper end of each of the slopes 112a and 112b. The guiding member 114 has a top face forming a slope that is continuous to the slope of the holding member 111. Stoppers 115 are attached to the lower ends of the slopes 112a, 112b, respectively. The stoppers 115 are configured to normally project toward each other by an biasing force of a spring (not shown) to catch the vial 9 sliding down the slopes 112a, 112b, and to retract against the biasing force of the spring to allow the vial 9 to pass therethrough when an operator removes the vial 9.

Figure 15:
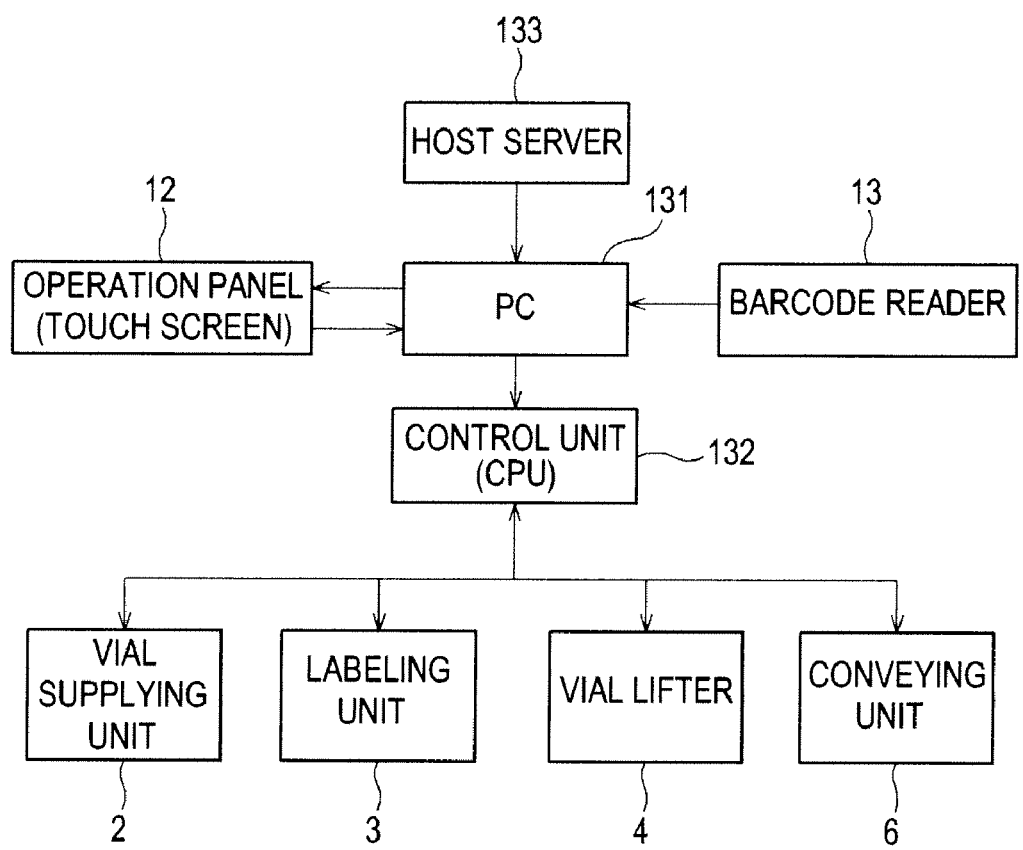
FIG. 15 is a block diagram of the tablet filling device.

FIG. 15 is a control block diagram of the tablet filling device 1 according to the present invention. The vial supplying unit 2, the labeling unit 3, the vial lifter 4, and the conveying unit 5 are controlled by a control unit 132 based on commands from a personal computer (PC) 131. Further, the personal computer 131 is managed by a host server 133. The personal computer 131 is configured to receive signals inputted from a touch screen of the operation panel 12 and to output display signals required for the operation panel 12. The personal computer 131 is further configured to receive read signals inputted from the barcode reader 13.

Operations of the tablet filling device 1 having the above-described configuration will now be described with reference to a flow chart illustrated in FIG. 16.

Figure 17:
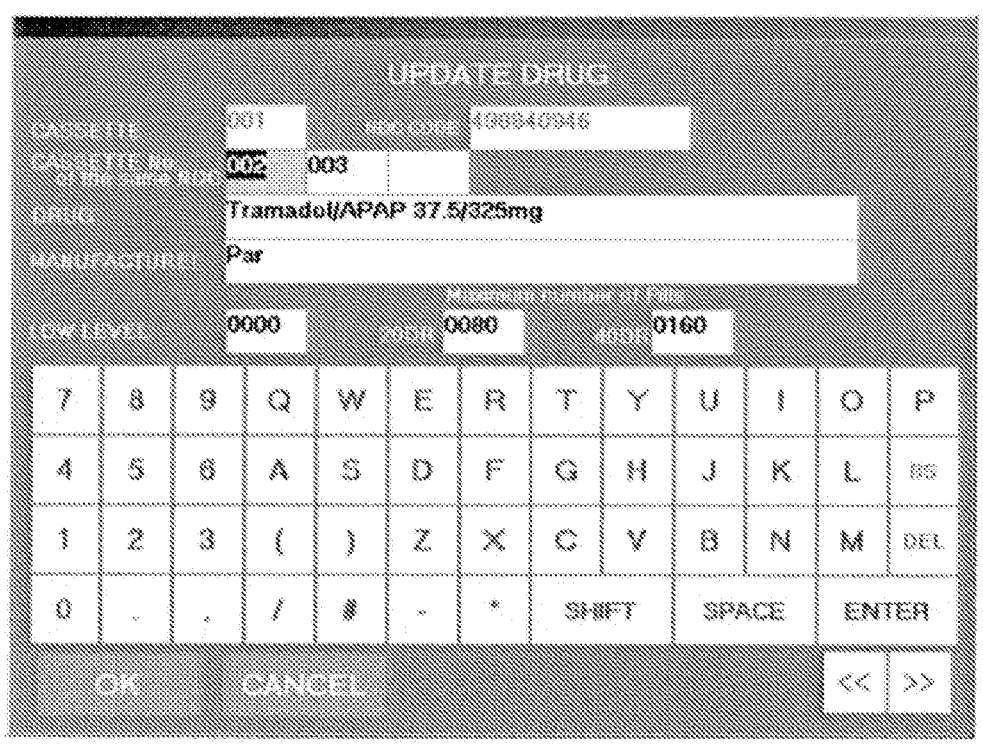
FIG. 17 illustrates a screen for setting a maximum filling quantity.

When a prescription data is received from the host server 133 at Step S1, the prescription data is processed to a dispensation data at Step S2. As to tablets, a vial order is given to the tablet filling device 1 at Step S3. As to injectable solutions, powdered medicines, heat tablets and the like, a dispensing order is given to respective devices at Step S4 and they are dispensed by the respective device or manually dispensed at Step S5. When the vial order is received, a proper vial 9 having a volume sufficient enough to accommodate the tablets is determined at Step S6, based on data of maximum filling quantity from the medicine master 134 of the personal computer 131. The medicine master 134 stores a maximum filling quantity of each tablet for a vial 9 according to data such as a shape, weight and volume of the tablet. The maximum filling quantity for the vial 9 is set through a screen illustrated in FIG. 17. In case of a tablet of "Tramado/APAP 37.5/325 mg" in an example illustrated in FIG. 17, the maximum filling quantity is set eighty for a vial 9 of 20DR and one hundred sixty for a vial of 40DR.

At Step S7, it is judged whether the determined vial 9 is of 20DR or 40DR. Where 40DR, it is judged at Step S8 whether the vial 9 of 40DR is out-of-stock based on a detection signal of the stockout sensor 29a of the stocker 21. When the vial 9 of 40DR is out-of-stock, a signal of error display (display indicating vial replenishment) is sent to the operation panel 12 at Step S9. As a result, a stockout warning indication is displayed on the operation panel 12 at Step S10.

Where the vial 9 is of 20DR at Step S7, it is judged at Step S11 whether the vial 9 of 20DR is out-of-stock based on the detection signal of the stockout sensor 29a of the stocker 21. When the vial 9 of 20DR is out-of-stock, it is further judged at Step S12 whether the alternative vial 9 of 40DR larger than that of 20DR is out-of-stock. When out-of-stock, the error display is ordered at Step S9 and then the stockout warning indication is displayed on the operation panel 12 at Step S10. When the alternative vial 9 of 40DR is not out-of-stock at Step S12, the previously determined size of the vial 9 is changed from 20DR to 40DR at Step S13. At Step S14, when the vial 9 of 40DR is not out-of-stock at Step S8, the size of the vial 9 is fixed as previously determined 40DR. Further, at Step S14, when the vial 9 of 20DR is not out-of-stock at Step S11, the size of the vial 9 is fixed as previously determined 20DR. Furthermore, at Step S14, when changed at Step S13, the size of the vial 9 is fixed as changed 40DR.

If the size of the vial 9 is fixed at Step S14 as described above, an operation of supplying the vial 9 starts at Step S15. First, the conveyor 23 and the removal device 24 of the stocker 21, in which the vials 9 of the fixed size are accommodated, are driven. Then, one of the vials 9 in the stocker 21 is removed by means of the paddle 25 of the removal device 24 and slides down the chute 27 to be placed on the forks 28. Further, the forks 28 are adjusted to have their gap correspond to the size of the vial 9. Thus, even if the vial 9 slides down the chute 27 with either its opening or bottom headed forward, the flange 9a is supported by the forks 28 with the opening facing upward.

Figure 16:
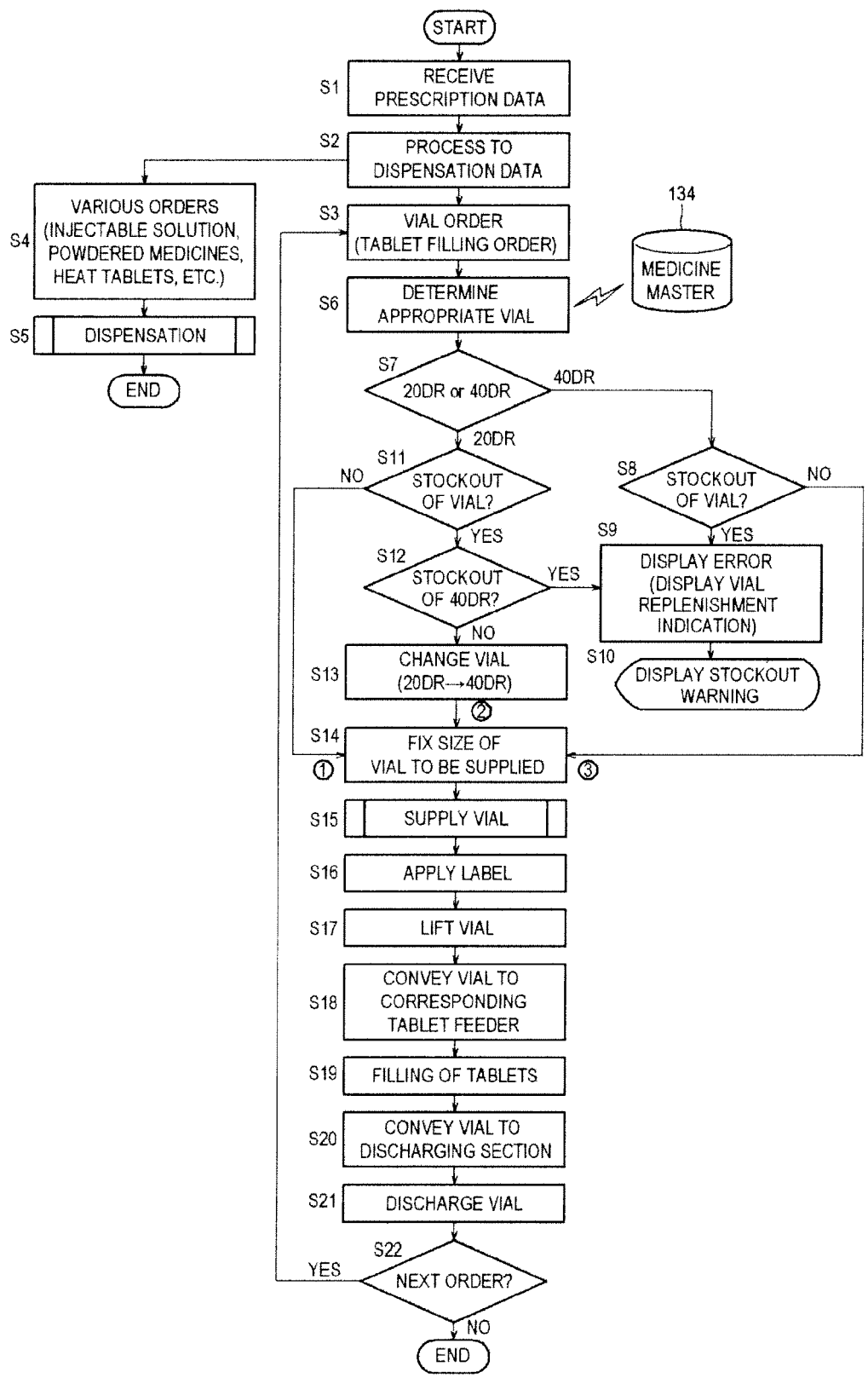
FIG. 16 is a flow chart showing operations of the tablet filling device.

When the vial supply operation is completed, an operation of applying the label 33 on the vial 9 is done at Step S16 of the flow chart illustrated in FIG. 16. First, the pusher 32 is driven to move the vial 9 supported by the forks 28 onto the supporting plate 52 of the vial lifter 4. Then, while the vial 9 is pushed against the driving roller 38 of the label printer 31 and is rotated, the label printer 31 is actuated. Thus, predetermined matters are printed on the label 33 of the label tape 34 as it passes through the print head 36. And, when the printed label 33 approaches the vial 9, it is removed from the label tape and is applied to the vial 9.

When the labeling operation is completed, an operation of lifting the vial 9 is done at Step S17 of the flow chart illustrated in FIG. 16. When the lifting table 51 is moved upward by means of the lifting mechanism 53, the pins 55 are inserted to the supporting plate 52 and the pin opening/closing bar 54 disengages from the movable blocks 56. Thus, the four pins 55 are moved by the biasing force of the springs 58 to grip the vial 9. As the lifting table 51 is further moved upward, the supporting plate 52 hung up by the bracket 61 is pushed up and the vial 9 is lifted up to a first delivery position of the conveying unit 6 and stops thereat. When the vial 9 is held by means of the conveying unit 6 at the first delivery position, the lifting table 51 is lowered. When the lifting table 51 comes near to a downward standby position, the pin opening/closing bar 54 engages the movable blocks 56, to which the four pins 55 are attached, to widen the space between the pins 55 against the biasing force of the springs 58. Then, the lifting table 51 waits so as to receive the next vial 9. During the downward movement of the lifting table 51, the supporting plate 52 is supported by the bracket 61 and only the lifting table 51 is lowered up to the standby position.

When the delivery operation associated with lifting of the vial 9 is completed, the conveying unit 6 is driven and then an operation of conveying the vial 9 to the tablet cassette 73 accommodating corresponding tablets is done at Step S18 of the flow chart illustrated in FIG. 16. First, the vertical rail 92 is forward and backward moved along the first horizontal rails 91 and the second horizontal rail 93 is vertically moved along the vertical rail 92, such that the arm unit 94 on the second horizontal rail 93 is brought into proximity to the vial 9 on the lifting table 51 and the arms 101 of the arm unit 94 grips the vial 9. Then, the vial 9 gripped by the arm unit 94 is brought into proximity to the tablet cassette 73 accommodating the corresponding tablets. Tilting of the tilting base 99 tilts the vial 9, thereby positioning the opening of the vial obliquely below the tablet outlet 74. As the arm unit 94 is advanced, the count sensor 104 is inserted to the sensor hole 104' of the supporting panel 71, and the detection rod 109 is inserted to the detection rod hole 109' of the supporting panel 71, and the protruding piece 108 is inserted to the protruding piece hole 108' of the supporting panel 71 to engage the engaging portion 84 of the tablet cassette 73, and the engaging portion 107 of the driving shaft 106 is inserted to the driving shaft hole 106' of the supporting panel 71 to engage the engaging receptacle 83 of the tablet cassette 73.

When the movement of the vial 9 is completed, an operation of accommodating the tablets is done at Step S19. As the motor 105 of the arm unit 94 is driven, the rotor 77 of the tablet cassette 73 rotates via the driving shaft 106, the worm gear 82, the intermediate gear 81, and the rotor gear 80. Thus, the tablets accommodated in the tablet container 76 and held in the pocket are accommodated by the vial 9 one by one from the discharging hole 78 through the tablet outlet 74 of the supporting panel 71. The tablets passing through the tablet outlet 74 are detected by the count sensor 104. If the vial 9 accommodates a predetermined number of tablets, then the vial is vertically held by returning the tilting base 99 to its horizontal state.

When accommodating the tablets is completed, at Step S20, the conveying unit 6 is driven to convey the vial 9 filled with the tablets to the discharging unit 7. In this case, the vial 9 is allowed to be positioned above the guiding members 114 of the holding members 111 of one of the outlets 113, in which the previously discharged vial 9 is not held. Further, it is judged whether a vial is held in the outlet 113 or not by an output signal from a vial detection sensor (not shown) disposed adjacent to the lower ends of the slopes 112a, 112b. Furthermore, the vial 9 of a small size is allowed to be positioned above the upper guiding members 114, while the vial 9 of a large size is allowed to be positioned above the lower guiding members 114.

When the movement of the vial is completed, at Step S21, the arms 101 of the arm unit 94 are opened to place the flange 9a of the vial 9 onto the guiding members 114 of the discharging unit 7. Thus, the vial 9 slides down along the slope 112a or 112b of a pair of the holding members 111 to be held in the outlet 113. Then, an operator can remove the vial 9.

Figure 19:
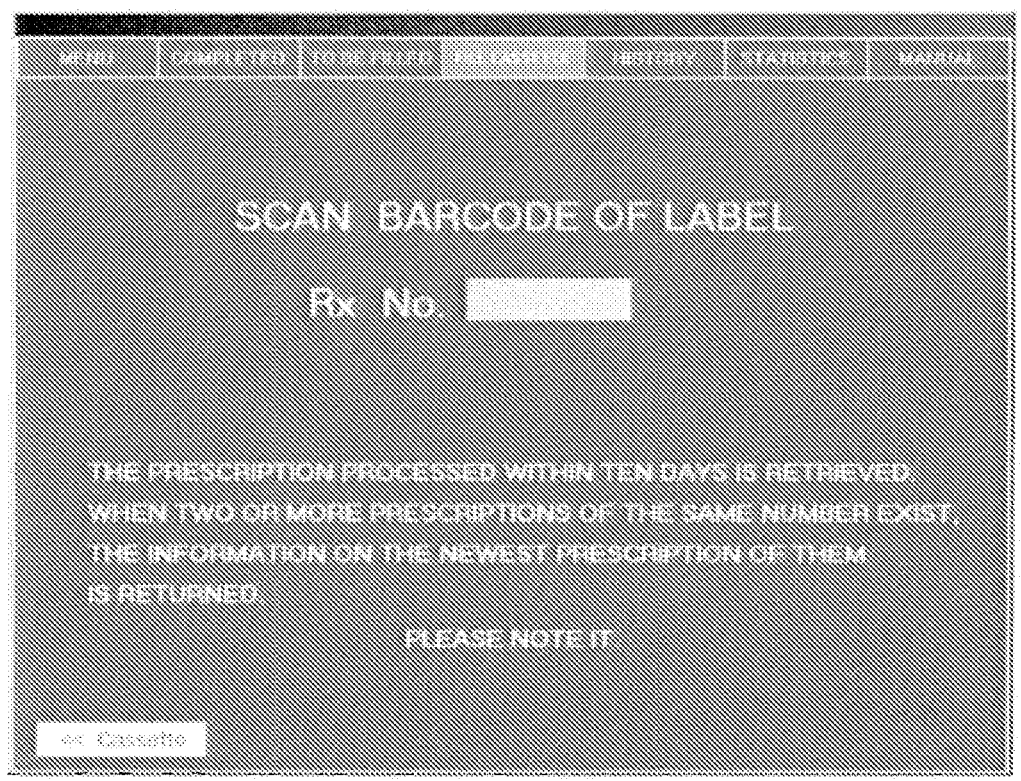
FIG. 19 illustrates a screen displayed in the operation panel during replenishing tablets.
Figure 20:
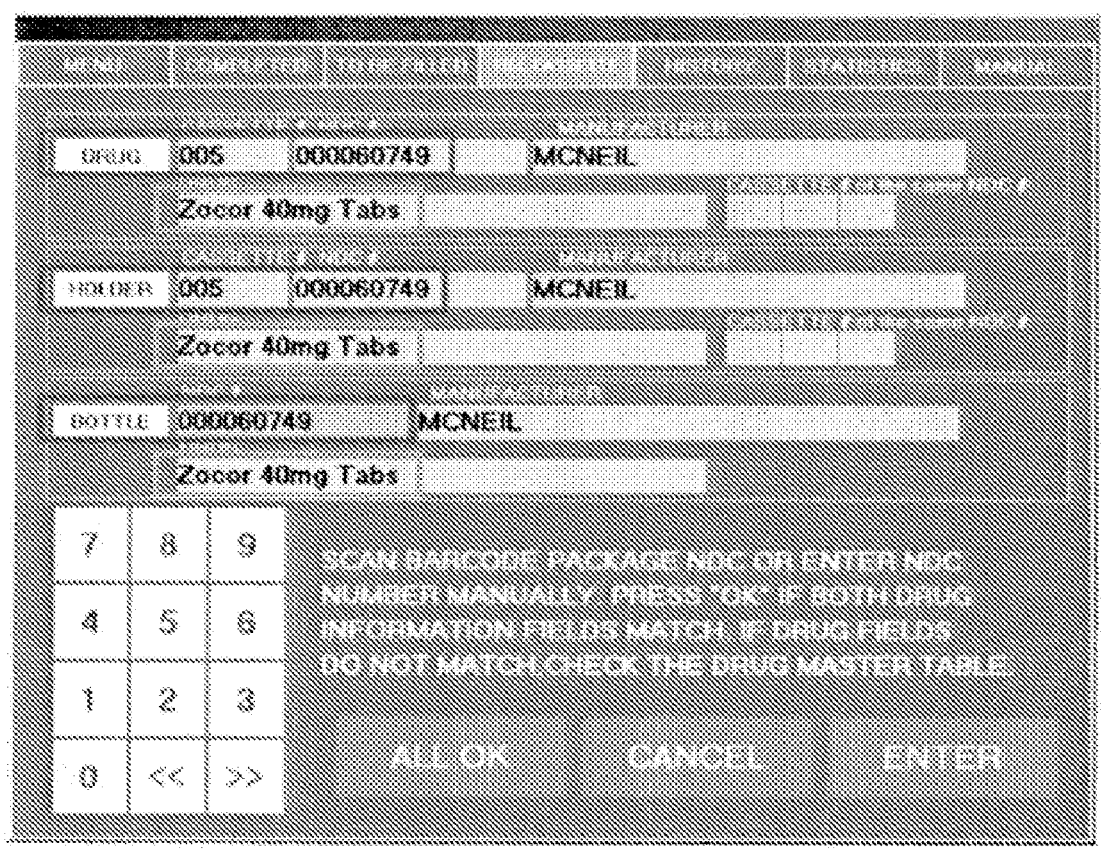
FIG. 20 illustrates a screen displayed in the operation panel during replenishing tablets.

Meanwhile, when the tablet cassette 73 runs short of the tablets, it is necessary to replenish the tablet cassette 73 with the tablets. Further, when the vial 9 is filled with the tablets irrelevant to the prescription, or when the tablets are exhausted during filling the vial with the tablets to thereby cause insufficient filling, it is necessary to return the tablets in the vial 9 to the tablet cassette 73. In case of replenishing tablets according to a prior art, a cassette number is inputted through a screen of an operating panel and a barcode of a medicine bottle box is scanned. And, if the medicine is coincidental, a tablet cassette corresponding to the cassette number is removed and then tablets of a medicine bottle are replenished. However, when a tablet cassette irrelevant to the inputted cassette number is erroneously removed, there is a problem in that the incorrect tablet cassette is refilled with the tablets. Further, similarly in case of returning the tablets in the vial to the tablet cassette, the tablets can be returned to the incorrect tablet cassette. Thus, according to this embodiment, in order to eliminate mistakes associated with replenishing or returning tablets, operations are done according to screens displayed in the operation panel 12 as illustrated in FIGS. 18 to 20.

Figure 18:
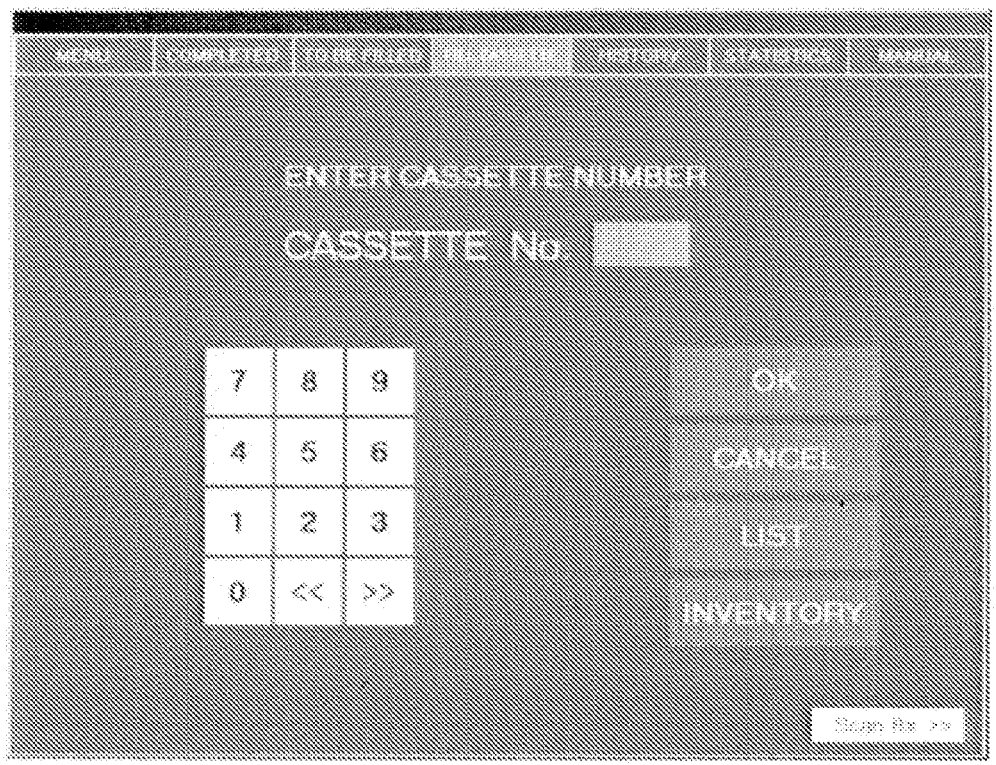
FIG. 18 illustrates a screen displayed in an operation panel during replenishing tablets.

When an item of "FILL CASSETTE" of a menu bar that is displayed in an initial screen of the operation panel 12 is clicked, an indication of "ENTER CASSETTE NUMBER" is displayed in the screen as illustrated in FIG. 18, and the number of an objective tablet cassette 73 is allowed to be entered. Subsequently, an indication of "SCAN BARCODE" is displayed in the screen as illustrated in FIG. 19. Thus, the barcode of the medicine bottle box is scanned by means of the barcode reader 13 in the event of replenishing tablets, whereas a barcode of the label of the vial is scanned in the event of returning tablets. When the objective tablet cassette 73 is mounted on the auxiliary mount 14 provided at the front of the device body 8, the barcode of the tablet cassette 73 is read out by a reader device provided in the auxiliary mount 14. As a result, as illustrated in FIG. 20, the entered cassette number and a medicine code, a maker and a medicine name of the tablets accommodated in the tablet cassette 73 of such a cassette number are displayed in an upper section. Further, a cassette number of the mounted tablet cassette 73, a medicine code, a maker and a medicine name of the tablets accommodated such a mounted tablet cassette are displayed in a medial section. Furthermore, a medicine code, a maker and a medicine name indicated by the barcode of the scanned medicine bottle box or the vial 9 are displayed in a lower section. If those informations are coincidental, an "OK" button may be pressed on. If not, it may be taken the following measure: that the tablet cassette 73 may be checked up and a correct one may be mounted on the auxiliary mount 14, or that the medicine bottle box may be checked up and a correct one may be scanned.

As described above, according to this embodiment, a tablet and a tablet cassette are checked up with each other based on three pieces of information such as the information on the entered cassette number, the information read out from the tablet cassette 73 mounted on the auxiliary mount 14, and the information scanned from the medicine bottle box or the vial, thereby avoiding replenishing an incorrect tablet cassette 73 with tablets or returning tablets to the incorrect tablet cassette.

Meanwhile, in the flow chart illustrated in FIG. 16, judging the stockout of the vial 9 (checking up the amount of stock) is carried out at Steps S8, S11 and S12 that are time points of the vial order. However, it should not be limited thereto. The judgment of the stockout of the vial 9 is necessary to be made also during sequential operations for tablet filling. For example, the error relating to label application may occur during applying the label 33 to the vial 9 at the labeling unit 3. Further, the stockout of the tablet may be detected during supplying the tablets to the vial 9 at the tablet supplying unit 5. When the error relating to label application occurs, it is necessary to apply the label 33 to a new vial 9. In this case, it may be judged whether the new vial 9 is out-of-stock when the new vial 9 is removed. Further, when the stockout of tablet occurs during supply of the tablets, it is necessary to fill a new vial 9 with the tablets after the tablet cassette 73 are replenished with the tablets. In this case, it may be judged whether the new vial 9 is out-of-stock when the new vial 9 is removed. Then, the size of such a vial may be fixed through the same Steps as Step 8 to Step 14 in the foregoing embodiment as illustrated in FIG. 16.

The invention claimed is:

1. A method of removing a vial from a stocker accommodating a large number of vials according to a prescription data, dispensing tablets into the vial to fill the vial and discharging the vial filled with the tablets, comprising:
   determining a vial of an appropriate size according to the prescription data;
   checking for a stock of the determined vial;
   fixing a size by changing the determined vial to a vial of a size larger than that of the determined vial if the vial of the determined size is out-of-stock; and
   discharging the vial filled with the tablets to one of two slopes, the two slopes forming an outlet and being juxtaposed vertically, the one of the two slopes holding the vial of the fixed size.

2. The method of claim 1, wherein checking for a stock of the determined vial is performed in at least one of the following:
   when an error relating to label application occurs during applying a label to the vial; and
   when it is detected that the tablets are out-of-stock during supplying the tablets to the vial.

* * * * *